US 008845615B2

(12) United States Patent  (10) Patent No.: US 8,845,615 B2
Nelson  (45) Date of Patent: Sep. 30, 2014

(54) CLAMPING CATHETER CONNECTORS, SYSTEMS, AND METHODS

(75) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 455 days.

(21) Appl. No.: 13/091,532

(22) Filed: Apr. 21, 2011

(65) Prior Publication Data

US 2011/0270231 A1    Nov. 3, 2011

Related U.S. Application Data

(60) Provisional application No. 61/329,329, filed on Apr. 29, 2010.

(51) Int. Cl.
*A61M 25/18* (2006.01)
*A61M 25/00* (2006.01)

(52) U.S. Cl.
CPC .................................. *A61M 25/0014* (2013.01)
USPC ............................................ 604/535; 604/177

(58) Field of Classification Search
CPC ...................... F16L 33/222; A61M 2039/1027; A61M 2039/1066; A61M 2209/04; A61M 25/0014; A61M 27/002; A61M 39/1011; A61M 39/12
USPC ........................... 604/535, 174–180, 533–284
See application file for complete search history.

(56) References Cited

U.S. PATENT DOCUMENTS 1,113,080 A * 10/1914 Wilson ........................... 285/243
3,447,819 A    6/1969 Borsum et al.
3,482,857 A   12/1969 Gohs
4,013,310 A    3/1977 Dye
4,192,532 A    3/1980 Pacella
4,334,551 A    6/1982 Pfister
4,405,163 A    9/1983 Voges et al.
4,526,572 A    7/1985 Donnan et al.
4,592,749 A    6/1986 Ebling et al.
4,610,468 A    9/1986 Wood
4,632,435 A   12/1986 Polyak
4,636,204 A    1/1987 Christopherson et al.
4,691,943 A    9/1987 DeLand et al.
4,704,103 A   11/1987 Stöber et al.
4,834,719 A    5/1989 Arenas
4,890,866 A    1/1990 Arp (Continued)

FOREIGN PATENT DOCUMENTS

EP    1 466 645 A2   10/2004
EP    1 466 645 A3    4/2005

(Continued)

OTHER PUBLICATIONS

U.S. Appl. No. 12/770,292, filed Apr. 29, 2010, Sage et al.

(Continued)

*Primary Examiner* — Kevin C Sirmons
*Assistant Examiner* — Phillip Gray

(57) ABSTRACT

Catheter connectors, systems, and methods in which one or more catheters are attached to a connector. In the illustrated embodiment, the catheter is retained relative to the connector by inward radial compression between an outer surface of a hollow connector pin inserted into the catheter, and a clamping arm that pivots relative to the connector pin and pushes against an outer surface of the catheter. One or more sleeves may slide over the clamping arm to bias the clamping arm radially inwardly.

13 Claims, 4 Drawing Sheets

(56) References Cited

U.S. PATENT DOCUMENTS

| | | |
|---|---|---|
| 4,895,570 A | 1/1990 | Larkin |
| 4,929,236 A | 5/1990 | Sampson |
| 4,994,048 A | 2/1991 | Metzger |
| 5,209,740 A | 5/1993 | Bryant et al. |
| 5,290,253 A | 3/1994 | Kira |
| 5,405,339 A | 4/1995 | Kohnen et al. |
| 5,456,676 A | 10/1995 | Nelson et al. |
| 5,613,945 A | 3/1997 | Cai et al. |
| 5,637,102 A | 6/1997 | Tolkoff et al. |
| 5,913,852 A * | 6/1999 | Magram ............ 604/540 |
| 6,402,207 B1 | 6/2002 | Segal et al. |
| 6,456,676 B1 | 9/2002 | O'Connor et al. |
| 6,506,182 B2 | 1/2003 | Estabrook et al. |
| 6,517,115 B1 | 2/2003 | Blivet |
| 6,554,802 B1 | 4/2003 | Pearson et al. |
| 6,641,177 B1 | 11/2003 | Pinciaro |
| 6,796,586 B2 | 9/2004 | Werth |
| 6,817,995 B1 | 11/2004 | Halpern |
| 6,910,906 B2 | 6/2005 | Schorn |
| 6,971,390 B1 | 12/2005 | Vasek et al. |
| 6,997,919 B2 | 2/2006 | Olsen et al. |
| 7,331,613 B2 | 2/2008 | Schulte |
| 7,387,624 B2 * | 6/2008 | Nelson ............ 604/536 |
| 7,537,245 B2 | 5/2009 | Cross, Jr. |
| 7,678,101 B2 | 3/2010 | Sage |
| 2003/0181849 A1 | 9/2003 | Castellanos |
| 2004/0039373 A1 | 2/2004 | Harding et al. |
| 2004/0204690 A1 | 10/2004 | Yashiro et al. |
| 2005/0033371 A1 | 2/2005 | Sommer et al. |
| 2005/0085794 A1 | 4/2005 | Denoth et al. |
| 2005/0107739 A1 | 5/2005 | Palma |
| 2005/0137614 A1 | 6/2005 | Porter et al. |
| 2005/0251102 A1 | 11/2005 | Hegland et al. |
| 2008/0103476 A1 | 5/2008 | Schulte |
| 2008/0275427 A1 | 11/2008 | Sage |
| 2008/0275429 A1 | 11/2008 | Sage |

FOREIGN PATENT DOCUMENTS

| | | |
|---|---|---|
| EP | 1 501 583 B1 | 5/2006 |
| EP | 1 466 645 B1 | 8/2007 |
| GB | 2 318 846 A | 5/1998 |
| WO | WO 94/23775 A1 | 10/1994 |
| WO | WO 97/25562 A1 | 7/1997 |
| WO | WO 03/030985 A2 | 4/2003 |
| WO | WO 03/030985 A3 | 7/2003 |

OTHER PUBLICATIONS

U.S. Appl. No. 61/329,329, filed Apr. 29, 2010, Brian D. Nelson.

* cited by examiner

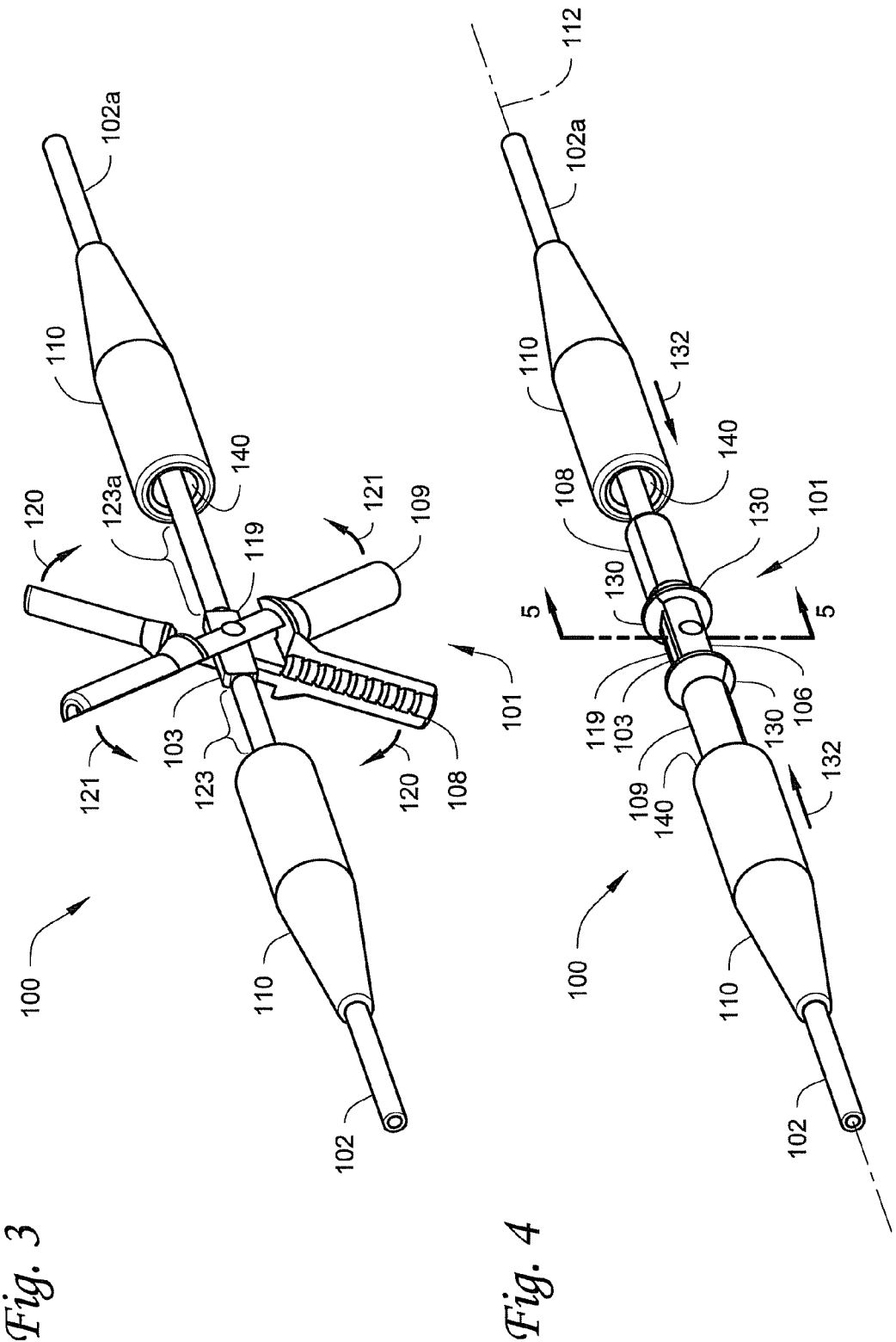

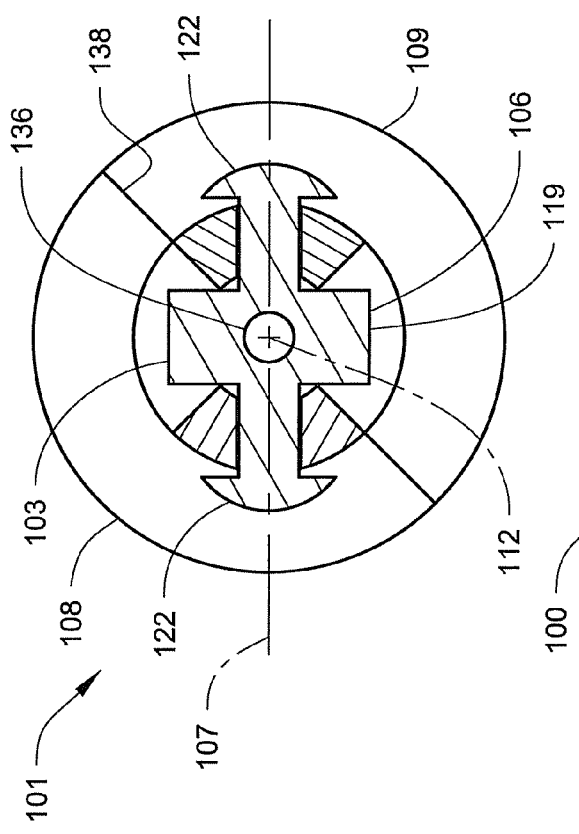
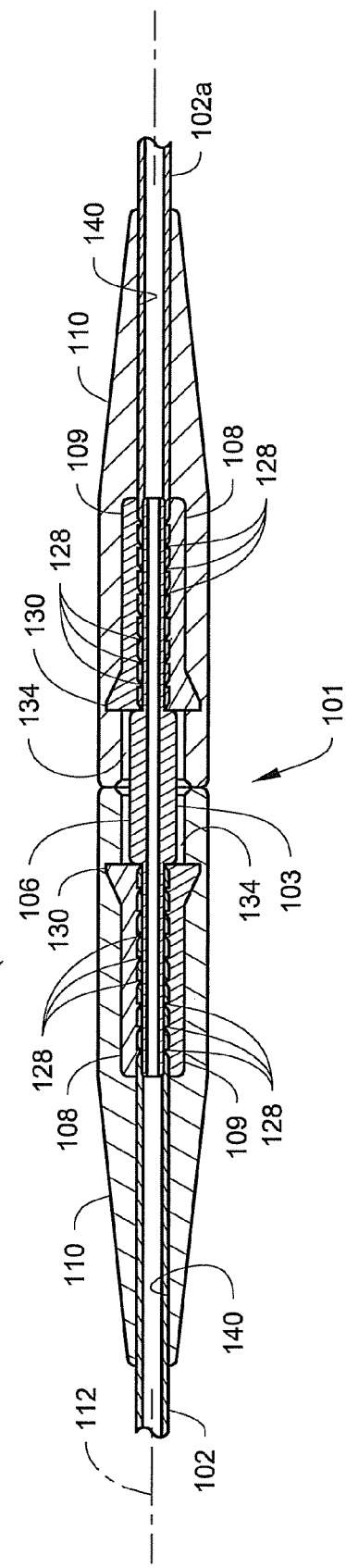
Fig. 5
Fig. 6

CLAMPING CATHETER CONNECTORS, SYSTEMS, AND METHODS

RELATED APPLICATION(S)

This application claims the benefit of U.S. Provisional App. No. 61/329,329, filed Apr. 29, 2010, the content of which is incorporated herein by reference in its entirety.

TECHNICAL FIELD

Embodiments of the present invention relate generally to medical connection systems and, more particularly, to connectors, systems, and methods for coupling a catheter to another catheter or to a medical device.

BACKGROUND

In many medical applications, it is necessary to connect one section of medical tubing, e.g., a catheter, with a device or another catheter. Generally speaking, it is important that these connections be relatively secure and stable so that the catheter does not separate or develop leaks. Security and leak-resistance take on elevated importance in applications where the catheters are implanted within a human body.

One procedure that necessitates implantation of a catheter into the body involves the use of an implantable medical device, e.g., a drug infusion pump. Such implantable medical devices are often used to control pain and/or spasticity, as well as to provide one or more drugs or fluid medications to a particular location within the body. A typical implant procedure may involve implanting a drug infusion pump into a cavity or subcutaneous pocket in the body and delivering a drug, via one or more catheters, to an epidural space or intrathecal space of the spinal column, or to a particular location within the brain.

An exemplary procedure may include positioning a first catheter at the desired location in the body and then connecting the first catheter to a second catheter via a connector. The connection may be made by inserting one end or pin of the connector into a lumen of one catheter and the other end of the connector into the lumen of the other catheter and then sliding both catheters towards one another (towards the middle of the connector). The second catheter may have its opposite end connected to the drug infusion pump. The ends of the pin may have a larger outer diameter than the mating inner diameter of the catheters. To increase the holding/sealing force in these connector configurations, the interference between the pin and the catheter is typically increased. The pin may also incorporate barbs to increase axial holding capacity. While increased interference between the catheter and the pin may improve axial catheter holding force and leak pressure performance, it may also make it more difficult to push the pin into the catheter, especially in a wet surgical environment. Thus, to accommodate desirable catheter attachment forces, axial holding capacity and/or leak performance are sometimes sacrificed.

While adequate, difficulties have been encountered in the manufacture and use of such connectors. For example, one or both of the catheters may incorporate a braid in the catheter wall. The braid may provide various benefits including, for example, increased radial, longitudinal, and torsional stiffness. While these attributes are beneficial, the braid may also limit the expansion capacity of the catheter(s), making it difficult to achieve the desired level of interference. Moreover, even without braided catheters, these connectors, which have been sized to fit within the lumens of the receiving catheters, are small and may be difficult to manipulate by a clinician during implantation (e.g., in a wet, surgical environment). As a result, increasing the interference between the connector and the catheter may not be desirable. Other potential problems may include a lack of ability to adequately secure the catheters relative to the connector; and an inability to provide sufficient strain relief to the catheters. These issues may result in a weakened connection that is susceptible to catheter separation and/or leakage.

SUMMARY

The present invention provides catheter connectors, connection systems, and methods in which the mechanism for axially securing and/or sealing a catheter relative to a connector may be de-coupled from the catheter connection procedure. For instance, catheter holding barbs may be moved off of the connector pin and located on a clamping member that itself acts upon an outer surface of the catheter after the catheter has been attached to the connector. Thus, axial catheter holding force and leak performance may be substantially increased by not only relying on the radial interference between the connector pin and the catheter, but by an additional external clamping force applied from a strain relief member that is assembled after the initial catheter/connector pin connection is made.

In one embodiment, a catheter connection system is provided and includes: a tubular connector pin having an engagement portion configured for insertion into a lumen of a catheter; and at least one clamping arm movably attached to the connector pin. The clamping arm is movable from a first position, wherein a clamp portion of the clamping arm extends outwardly and away from the engagement portion of the connector pin, to a second position, wherein the clamp portion is positioned along and in close proximity to the engagement portion. A tubular sleeve is also provided and is movable along a longitudinal axis of the connector pin to a locked position wherein, when the clamping arm is in the second position and the sleeve is in the locked position, a lumen of the sleeve receives the clamping arm with interference and holds the clamping arm in the second position relative to the engagement portion of the connector pin.

In another embodiment, a catheter connection system is provided that includes a catheter defining a lumen, the catheter comprising a first end. A tubular connector pin is also included and has an engagement portion configured for insertion into the lumen at the first end of the catheter such that a first portion of the catheter surrounds the engagement portion. Two clamping arms are pivotally attached to the connector pin. Each of the two clamping arms are pivotable from a first position, wherein a clamp portion of each of the two clamping arms extends outwardly and away from the engagement portion of the connector pin, to a second position, wherein the clamp portion of each of the two clamping arms is positioned to lie along the first portion of the catheter. A tubular sleeve is also included and is positionable, when both of the two clamping arms are in the second position, in a locked position wherein the sleeve surrounds each of the two clamping arms and biases the clamp portions of each of the two clamping arms against the first portion of the catheter and towards the engagement portion.

In yet another embodiment, a catheter connection system is provided that includes a first catheter and a second catheter each defining a lumen, each catheter comprising a first end. A connector body is also included and has an elongate, tubular connector pin with a first engagement portion and a second engagement portion, the first and second engagement portions insertable into the lumens of the first and second catheters, respectively. Two clamping arms are pivotally attached near their respective midpoints to the connector pin and configured to pivot about a pivot axis located between the first and second engagement portions. Each of the two clamping arms are pivotable in opposite directions between a first position, wherein first and second clamp portions of each of the two clamping arms extend outwardly and away from the first and second engagement portions, respectively, to a second position, wherein the first and second clamp portions of each of the two clamping arms contact the first and second catheters, respectively. First and second tubular sleeves are also included. The sleeves are each slidable along a longitudinal axis of the connector pin to a locked position wherein the first and second sleeves are positioned over the first and second clamp portions, respectively, when both of the two clamping arms are in the second position. As a result, a lumen of each sleeve receives the two clamping arms with an interference fit and biases the two clamping arms inwardly to compress the first and second catheters against the first and second engagement portions of the connector pin, respectively.

In still yet another embodiment, a method of connecting a catheter to a tubular member within a wet surgical environment is provided. The method includes inserting an end of a connector pin of a connector body into a lumen of a catheter. The connector body further includes first and second clamping arms pivotally attached to the connector pin for pivoting about a pivot axis passing through the connector pin. The method also includes pivoting the first and second clamping arms about the pivot axis until clamp portions of the first and second clamping arms extend along and contact a portion of the catheter that contains the pin. The method also includes sliding a tubular sleeve to a locked position over the clamp portions of the first and second clamping arms, the sleeve engaging the clamp portions with an interference fit.

The above summary is not intended to describe each embodiment or every implementation of the present invention. Rather, a more complete understanding of the invention will become apparent and appreciated by reference to the following Detailed Description of Exemplary Embodiments in view of the accompanying figures of the drawing.

BRIEF DESCRIPTION OF THE VIEWS OF THE DRAWING

The present invention will be further described with reference to the views of the drawing, wherein:

FIGS. 2A-2B illustrate exemplary implantable applications incorporating a connector/system/method in accordance with embodiments of the present invention, wherein;

FIG. 2A illustrates an implantable therapeutic delivery system with an exemplary double-sided connector; and FIG. 2B illustrates a delivery system with an exemplary single-sided connector;

FIG. 3 is a perspective view of the connector of FIG. 1 after attachment of two catheters, the connector shown with clamping arms in a first or open position;

FIG. 4 is perspective view of the connector of FIG. 3 after movement of the clamping arms of the connector to a second or closed position;

FIG. 5 is an cross section view of the connector of FIG. 4 taken along line 5-5 of FIG. 4; and FIG. 6 is a section view of the connector of FIG. 1 when fully assembled, e.g., with sleeves of the connector shown in a locked position.

Figure 1:
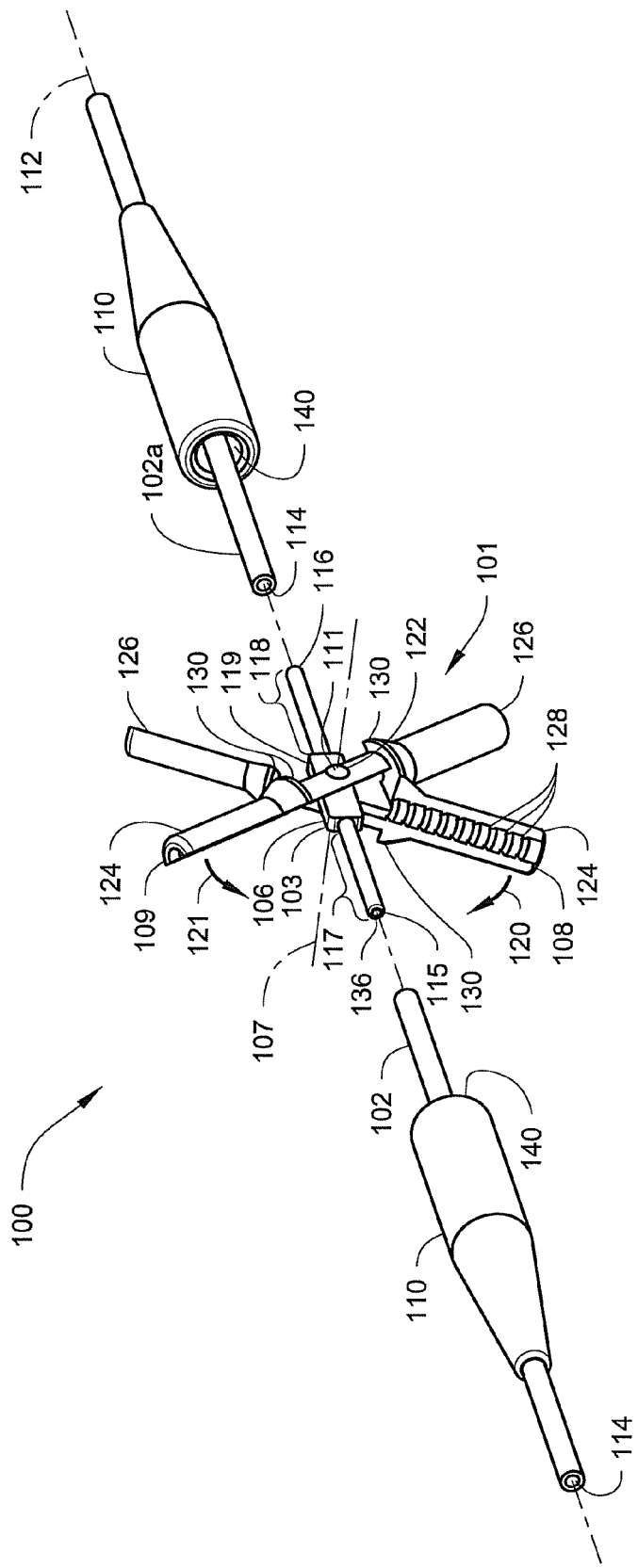
FIG. 1 is a perspective view of a catheter connection system utilizing a connector in accordance with one embodiment of the present invention.

The figures are rendered primarily for clarity and, as a result, are not necessarily drawn to scale.

DETAILED DESCRIPTION OF ILLUSTRATIVE EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

As used herein, "a," "an," "the," "at least one," and "one or more" are used interchangeably. The term "and/or" (if used) means one or all of the listed elements or a combination of any two or more of the listed elements. Moreover, where convenient, similar or identical components that are identified with the same reference numeral may be distinguished with the suffix "a" (e.g., 102a). It is understood that a component having such a suffix is, however, similar or identical to the component without the suffix. Further, the description of a component (e.g., catheter 102) provided herein is understood, unless otherwise stated, to apply to both components (e.g., both to the component without the suffix (102) and to the component with the suffix (102a)).

Illustrative embodiments of the present invention include a tubing (e.g., catheter) connector and system for coupling one or more sections of tubing, and to methods for using the same. In one embodiment, the connector provides a pin that may fit into each tubing section. A clamping arm associated with the pin may be selectively located over the pin and the section(s) of tubing into which the pin extends. One or more tubular sleeves may then be located to surround the clamping arm. The sleeve, via the clamping arm, may compress the sections of tubing against the pin, thereby providing a radial compressive force to seal and secure the tubing to the pin. In one embodiment, interlocking of the sleeve with the clamping arm may occur without the use of tools. Embodiments of the components, connectors, and systems described herein may be sized for implantation within a typical human or other mammalian body.

FIG. 1 is a perspective view of a catheter connection system 100 in accordance with one embodiment of the invention. As shown in this figure, the system 100 may include a connector 101 that securely interconnects a first medical tube, e.g., first or delivery catheter 102, with a second medical tube, e.g., second or therapy catheter 102a, both catheters of which may optionally form part of the system 100. The exemplary connector 101 may include a connector body 103 (that itself includes an elongate tubular connector pin 106 and one or more associated clamping arms (e.g., arms 108 and 109) movably attached to the pin) and one or more tubular connector sleeves 110. The arms 108, 109 are, in one embodiment, pivotable about a pivot 111 that defines a common pivot axis 107 passing through the pin 106 and that is normal to a longitudinal axis 112 of the pin. The arms may be configured to surround at least a portion of the catheter(s) 102 that overlap or contain the connector pin 106 via a scissoring action as further described below. The components 102, 106, 108, 109, and 110 may, when assembled, lie generally along or about the longitudinal axis 112 as shown in FIG. 6.

Although the system 100 is illustrated in FIG. 1 as embodied in a two-sided connector, i.e., the connector 101 includes a sleeve 110/arms 108, 109 on each of two opposite ends, other embodiments may utilize a connector having a sleeve and arm(s) on only one end without departing from the scope of the invention.

Figure 2A:
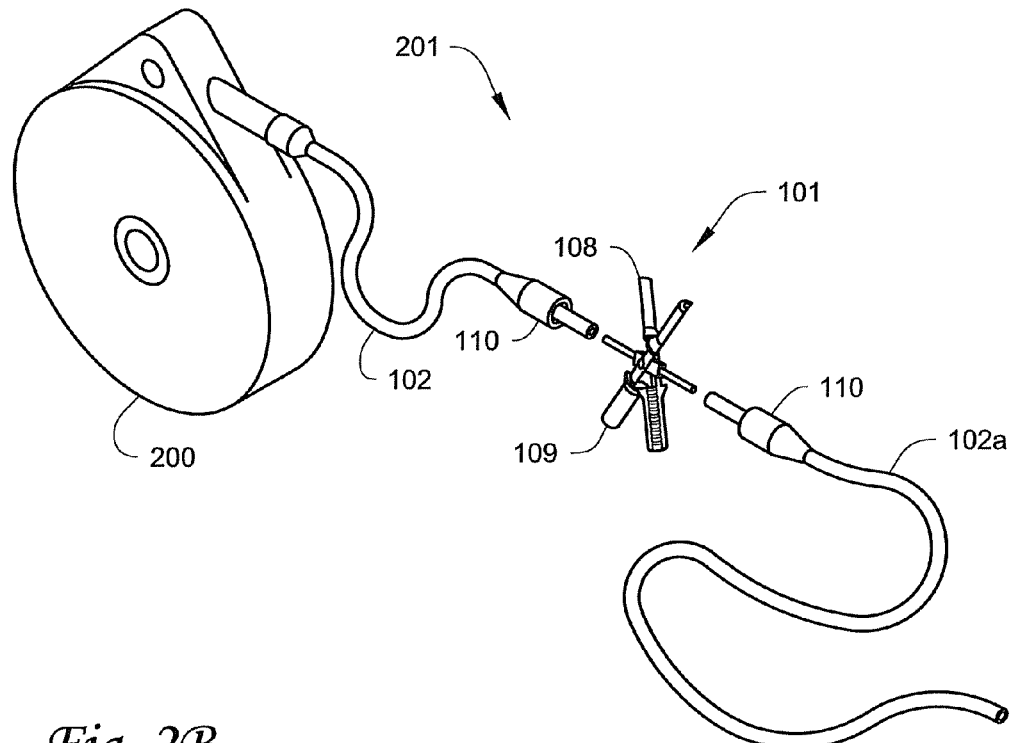
Figure 2B:
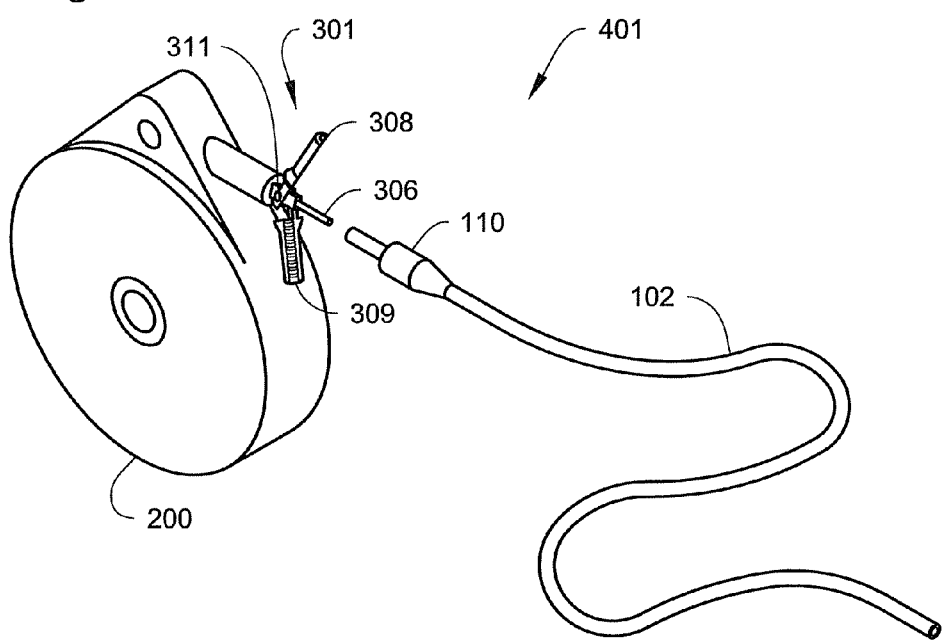

An exemplary two-sided connector 101 may be used to, for instance, couple two catheters together, e.g., first and second catheters 102, 102a that then couple an implantable medical device (e.g., an implantable infusion pump 200 such as a SynchroMed® II programmable infusion pump distributed by Medtronic, Inc., of Minneapolis, Minn. USA) to a remote drug delivery site as shown in the therapeutic substance delivery system 201 of FIG. 2A. A single-sided connector 301 may, on the other hand, be utilized to connect a component, e.g., the pump 200, to a catheter (catheter 102) as shown in the delivery system 401 of FIG. 2B. In case of the latter, the connector 301, e.g., a pin 306, may be an integral component of the pump 200 or otherwise be attached to the pump, and the arms 308, 309 may terminate at or near a pivot 311. The connector 301 may otherwise be constructed and operate in a manner similar to that of the connector 101 (e.g., utilize a sleeve 110) described in more detail below.

In yet other embodiments of the present invention, a connector system could be configured as a two-sided connector, but include different connector structures on each side. For example, one side of the connector may be configured in accordance with an embodiment of the present invention, while the other side of the connector may include an entirely different connector structure.

In still yet other embodiments, the connector may include more than two sides. For instance, the connector body could form a "Y"-connector including three or more sides, one or more of which may be a connector in accordance with an embodiment of the present invention.

FIG. 1 illustrates a perspective view of the exemplary connector 101 and connection system 100 prior to assembly (e.g., prior to attachment of the catheters). While the pin 106 and sleeves 110 (as well as the remaining components of the connection system 100) are shown as having a generally circular cross-sectional shape, any suitable cross-sectional shape could be utilized (e.g., octagonal, elliptical, oval, etc.) without departing from the scope of the invention.

As discussed herein, the illustrated system 100 includes a catheter (102, 102a) extending from both sides of the connector (although, once again, single and other multi-sided connectors are possible within the scope of the invention). For brevity, however, the description of the connector 100 may, where appropriate, focus on a single side, with the understanding that the opposite side, if present, is similar or identical.

Each catheter 102 may be of conventional construction, e.g., an elastomeric tubular body made from a polymer (pure or blended), silicone, urethane, or the like. Each catheter may include a first end, a second end, and a lumen 114 extending between the first and second ends such that fluids may be delivered through the catheter from one end to the other. One or both catheters may include features, e.g., strengthening braids, multiple layers, additives, etc., to satisfy the particular requirements of the intended application. That is, the construction of the catheters may vary without departing from the scope of the invention.

In the illustrated embodiment, the pin 106 is a hollow tubular member having a first end 115, a second end 116, and an enclosed lumen 136 or passageway extending between the ends. The pin may further define a first engagement portion 117 near the first end 115, and in the two-sided illustrated embodiment, a second engagement portion 118 on a side opposite the first engagement portion, e.g., near the second end 116 (the pin may include only a single engagement portion when configured as a single-sided connector as described above). Once again, while illustrated as cylindrical, the pin may have other shapes without departing from the scope of the invention.

The pin 106 may further include a central portion 119, which in the illustrated embodiment, is located between the first and second engagement portions. The central portion 119 may be enlarged as compared to the first and second engagement portions 117, 118 as illustrated. This enlarged aspect may be provided to accommodate pivotal mounting of the clamping arms 108 and 109 as further described below. Moreover, while the central portion 119 is illustrated as generally box-shaped, such a configuration is not limiting as it could assume most any shape that accommodates the pivotal connection of the arms 108, 109. For instance, the central portion 119 could be disk-shaped, wherein the pivot structure for the arms is formed on the two parallel faces of the disk.

Each engagement portion 117, 118 of the pin 106 may be configured for insertion into the lumen 114 of the respective catheter 102 so that that a portion (e.g., first portion 123 illustrated in FIG. 3) of each catheter surrounds or overlaps with its respective engagement portion. As further shown in FIG. 1, the first and second engagement portions 117, 118 may provide a chamfered or rounded nose and a featureless cylindrical surface to permit relatively smooth insertion of the engagement portions of the pin 106 into the respective catheters 102, 102a.

The diameters of the engagement portions 117, 118 may be selected to provide a minimal interference fit with the lumens 114 of the catheters so that the connector may be easily inserted into the catheters in a wet surgical environment. For example, when using a catheter made of silicone and having an undeflected inner diameter (ID) of about 0.025 inches (in) (about 0.6 millimeters (mm)) and an outer diameter (OD) of about 0.05 in (about 1.3 mm), the diameter of the engagement portions 117 and 118 may be about 0.028 in (about 0.7 mm) (once again, these dimensions are exemplary only as components of most any size/configuration are possible without departing from the scope of the invention). As further described below, the connector 101 may accomplish sealing and securing of the catheters 102 via other mechanisms in addition to the interference between the engagement portion(s) and the catheter(s).

The pin may be made of most any biocompatible material that provides the necessary rigidity and prevents occlusion under normal operating conditions. In one embodiment, the pin is constructed of titanium.

Each clamping arm 108, 109 may be permanently attached to the connector pin, e.g., pivotally attached to the pin at the pivot 111 such that it can rotate or pivot about the pivot axis 107. As used herein, the phrase "permanently attached" indicates that the arms 108, 109 are attached to the connector pin 106 during the manufacturing process and are not easily removed from the pin without tools or without damaging one or more components of the connector. In the illustrated embodiment, the arms 108 and 109 may be identical components.

To provide the desired clamping action, the arms 108, 109 may pivot, relative to the connector pin, in opposite directions about the pivot axis 107, e.g., the arm 108 may pivot in a clockwise (in FIG. 1) direction 120, while the arm 109 may pivot in a counterclockwise direction 121. The arms may pivot between a first position, wherein first and second clamp portions of each of the two clamping arms extend outwardly and away from the first and second engagement portions, respectively (see, e.g., FIGS. 1 and 3), to a second position, wherein the first and second clamp portions of each of the two clamping arms contact the first and second catheters, respectively (see, e.g., FIG. 4).

In the two-sided connector illustrated in FIGS. 1, 2A, and 3-6, each of the two clamping arms 108, 109 are pivotally attached near their respective midpoints to the connector pin 106. Moreover, each of the arms may include a first clamp portion 124 as shown in FIG. 1 to engage the respective catheter 102 as described below. Each of the arms may also include a second clamp portion 126 located on a side of the midpoint opposite the first clamp portion. As a result, the two clamping arms may be pivotally attached, near their respective midpoints, to the connector pin for pivoting about a pivot axis (e.g., axis 107) that is located between the first and second engagement portions 117, 118.

While the pivot 111 (e.g., pivot axis 107) may be formed in most any acceptable manner, it is in the illustrated embodiment, formed by one or more (e.g., two) shafts attached to the central portion 119. The shafts may protrude outwardly in a direction normal to the longitudinal axis 112 of the pin. Each of the arms 108, 109 may be secured to one of the shafts in any number of ways including, but not limited to, an E-Ring or C-Ring clip, a screw, or via a welding operation. In another embodiment, shaft/arm retaining could be achieved using a small shoulder bolt. In still yet another embodiment, a retaining head 122 (only one visible in FIG. 1) may be formed on the outer end of each shaft, e.g., via an orbital riveting process as is known in the art, to secure each arm to its respective pin. This latter configuration may be advantageous as it reduces separate parts that could inadvertently detach from the pin.

Once again, each clamping arm 108, 109 may be movable, e.g., pivotable, from the first position, wherein each clamp portion 124, 126 of the respective clamping arms extends outwardly and away from the engagement portion of the connector pin (as shown in FIG. 3), to the second position, wherein each clamp portion is positioned along and in close proximity to the engagement portion (see, e.g., FIG. 4). As a result, in the second position, the clamp portions 124, 126 of each clamping arm may be positioned to lie along the portion(s) 123 of the catheter(s) 102 that surrounds (i.e., overlaps) the engagement portion(s) of the connector pin.

As visible in the figures, the two clamping arms 108, 109 may each form meshing semi-cylindrical members that mate with one another along a plane. In the illustrated embodiment, the mating plane may both contain the longitudinal axis 112 of the connector pin 106 and may intersect the pivot axis 107 (e.g., the mating plane does not contain the pivot axis). As a result, by pivoting of the arms 108, 109 in opposing directions until they reach the second position illustrated in FIG. 4, the anus, e.g., the clamp portions 124 and 126, may combine to form substantially cylindrical members that surround the respective engagement portions 117 and 118 and the overlapping portions 123 of the catheters 102.

In the illustrated embodiment (see, e.g., FIG. 6), the clamping arms 108, 109 (when in the second position) may extend beyond the length of (e.g., beyond a distal end of) the connector pin 106 to provide a degree of strain relief to the catheters 102. However, embodiments wherein the pin is the same length, or even longer, than the clamping arms are certainly possible without departing from the scope of the invention.

An inner surface of the clamp portions (see, e.g., FIG. 1) may have formed thereon one or more surface disruptions, e.g., a plurality of inwardly protruding catheter-gripping barbs 128 (only visible on one clamp portion in this view, but see also FIG. 6). The barbs 128 may, when the arms are in the second position shown in FIGS. 4 and 6, permit the clamp portions 124, 126 to push or "bite" into the catheters 102 to provide adequate resistance to axial loads that would otherwise tend to pull the catheters away from the connector.

An outer or exterior surface of one or both of the clamping arms 108, 109 may also include a catch, e.g., radially protruding element 130 (e.g., rib or the like) operable to engage a portion of the sleeve 110 to axially retain the sleeve in a locked position as further described below. In the illustrated embodiment, wherein each arm may extend outwardly to each side of the pivot 111, each clamping arm may include two or more ribs (e.g., one on each side of the pivot as illustrated).

Like the connector pin 106, the clamping arms 108, 109 may be made from a variety of biocompatible materials. They are also, like the connector pin, made from a relatively noncompliant material, e.g., a material that is harder than the catheters, to ensure that the barbs 128 can effectively engage the catheters by pressing against the catheter outer surface. For instance, the arms may be made of titanium or a rigid thermoplastic such as polysulfone or polyetheretherketone (PEEK).

While the connector embodiments illustrated herein are shown with two arms 108, 109, embodiments configured with only a single arm are also contemplated within the scope of the invention. Single arm configurations may be useful where sufficient retention of the catheter may be achieved without fully surrounding the overlapping portion 123 of the catheter/pin with the arms.

The sleeves 110 may be separate components as illustrated in the figures. As further described below, they may be slid over proximal ends of the catheters 102 before the catheters are attached to the connector pin 106, as shown in FIG. 1, for reasons that will become apparent. Each sleeve 110 may be a tubular member that may slide not only over the catheters, but also over the clamping arms 108, 109 when the latter are in the second position illustrated in FIG. 4. The sleeves may be made from a relatively elastic, low-creep material including, for example, silicone and urethane. By utilizing an elastic material, the sleeves 110 may expand to fit over the clamping arms 108, 109, when in the locked position, whereby they may surround each of the two clamping arms (e.g., may be positioned over the first and second clamp portions) and apply a consistent inward, compressive radial force (a hoop stress) to the arms, thereby biasing the clamp portions of the arms towards the connector pin (e.g., against the first portions of the catheters 102 and towards the engagement portions 117, 118). This compressive radial forces acts to drive the barbs 128 into the outer diameter of the catheters, which squeezes the catheters against the pin 106, further increasing the axial holding force and leak performance of the system.

In use, the catheters may be implanted and tunneled (e.g., from the pump 200 of FIG. 2A and from the therapy delivery site) through the patient's body and cut to the appropriate length such that the proximal mating ends of the catheters 102, 102a are near one another and at the desired (e.g., subcutaneous) connector location. The sleeves 110 may then be passed onto the proximal ends of the catheters as shown in FIG. 1 and slid away from the ends sufficiently (e.g., to a first or unlocked position as shown in FIG. 1) to expose an adequate length of the catheters near their respective proximal ends.

As shown in FIG. 3, the catheters 102 and 102a may then be connected to the connector pin 106 by insertion of the first end 115 of the connector pin 106 into the lumen of the catheter 102 and the second end 116 into the lumen 114 of the catheter 102a until first portions 123, 123a of the catheters surround the respective engagement portions 117, 118 (see FIG. 1). Stated alternatively, each end of the pin 106 is configured for insertion into the lumen 114 of one of the catheters, and the lumen of each catheter is likewise configured to receive therein an end of its respective pin. As the pin is hollow (e.g., forms the enclosed lumen 136 along its entire length), fluids may thus flow from one catheter (e.g., catheter 102) through the pin to the other catheter (e.g., catheter 102a) when the connector is fully assembled. The insertion of the connector pin 106 into the catheters 102 may be conducted with the clamping arms 108, 109 in the first position as shown in FIGS. 1 and 3.

Once the catheters 102, 102a are adequately pressed onto the first and second engagement portions 117, 118, respectively (e.g., the engagement portions are inserted into the lumens until catheter ends are at or near the central portion 119 of the connector pin), the arms 108, 109 may be pivoted by the clinician about the pivot axis 107. As indicated in FIG. 3 and described above, the clamping arm 108 may pivot in the clockwise direction 120 while the arm 109 pivots in the counterclockwise direction 121.

When fully pivoted to the second position, the clamping arms 108, 109 lie parallel to the longitudinal axis 112 as shown in FIG. 4. As shown in this figure, the two clamping arms 108, 109 may pivot towards one another until the clamp portions 124, 126 extend along and contact the first portions 123 of the catheters 102 that contain the pin.

FIG. 5 illustrates a cross section of the connector 101 as taken along line 5-5 of FIG. 4. This view illustrates the construction of the shafts that retain the arms, and illustrates the arms 108, 109 when they are in the second position. FIG. 5 also illustrates the plane 138 along which the arms 108, 109 mate or approach one another.

At this point the clinician may slide the sleeves 110 towards the connector (towards one another and towards the locked position) as shown in FIG. 4, e.g., along the longitudinal axis 112 and in the direction 132. As the sleeves 110 are advanced, each sleeve may slide over the outer ends of the clamp portions of the clamping arms 108, 109. Each sleeve may include a lumen 140 fowling a mouth 134 (see FIG. 6), the mouth having an inner diameter that is smaller than the diameter of the clamping arms when the latter are in the second position and pressed into the catheters 102, i.e., the lumen 140 of each sleeve may receive the clamping arms with an interference fit. The resilient nature of the sleeves 110 may provide a consistent inward radial or hoop biasing force to the clamping arms 108, 109 and barbs 128 ensuring that the arms stay in contact with an outer surface of the catheters 102, 102a to compress the catheters against the engagement portions as illustrated in FIG. 6. This biasing force, in conjunction with the barbs 128, may provide substantial axial holding power to the catheters.

When the sleeves 110 are in the locked position of FIG. 6, the catches or ribs 130 formed on the outer surface of the clamping arms 108, 109 may protrude into the softer resilient wall of the sleeves. This engagement of the sleeves with the clamping arms may assist in axially securing the sleeves in the desired position relative to the connector body 103, e.g., relative to the clamping arms. In the illustrated embodiment, the ends of the sleeves are, when the sleeves are in the locked position, near the center of the pin 106 and may even abut one another. Such a configuration provides a soft and pliable, body-friendly implant surface over the entire connection.

While the exact size and length of the sleeves may be selected to accommodate most any particular application, each lumen 140 of the sleeve may, in one embodiment, have a diameter similar to an undeflected outer diameter of the associated catheter. Moreover, the sleeves 110 may extend beyond the ends of both the connector pin 106 and the clamping arms 108, 109 as shown in FIG. 6. This construction may further alleviate strain on the catheter during implantation.

Connectors and methods in accordance with embodiments of the instant invention may thus provide connecting mechanisms capable of maintaining a secure and leak-free pin-to-catheter connection without the need for maintaining a high degree of interference between the outer diameter of the pin and the lumen of the catheter. As shown in the illustrated embodiment, this may be achieved by a clamping mechanism that engages the catheter after attachment of the catheter to the pin. As a result, the force required to assemble the connection, e.g., the force required to slide the catheter onto the pin, may be minimized without sacrificing catheter retention effectiveness. Embodiments of the present invention may thus provide a reliable and secure catheter connection.

Illustrative embodiments of this invention are discussed and reference has been made to possible variations within the scope of this invention. These and other variations, combinations, and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A catheter connection system comprising:
   a catheter defining a lumen, the catheter comprising a first end;
   a tubular connector pin comprising an engagement portion configured for insertion into the lumen at the first end of the catheter such that a first portion of the catheter surrounds the engagement portion;
   two clamping arms pivotally attached to the connector pin about a pivot that defines a common pivot axis, each of the two clamping arms pivotable about the common pivot axis from a first position, wherein a clamp portion of each of the two clamping arms extends outwardly and away from the engagement portion of the connector pin, to a second position, wherein the clamp portion of each of the two clamping arms is positioned to lie along the first portion of the catheter; and
   a tubular sleeve positionable, when both of the two clamping arms are in the second position, in a locked position wherein the sleeve surrounds each of the two clamping arms and biases the clamp portions of each of the two clamping arms against the first portion of the catheter and towards the engagement portion.

2. The system of claim 1, wherein the two clamping arms pivot, relative to the connector pin, in opposite directions about the common pivot axis.

3. The system of claim 2, wherein each of the two clamping arms comprises a semi-cylindrical member that mates with the other of the two clamping arms along a plane that both contains a longitudinal axis of the connector pin, and intersects the common pivot axis.

4. The system of claim 2, further comprising two shafts protruding from the connector pin in a direction normal to a longitudinal axis of the connector pin, the two shafts defining the common pivot axis.

5. The system of claim 1, wherein each of the two clamping arms comprises catheter gripping barbs formed along an inner surface of the clamp portion.

6. The system of claim 1, wherein the two clamping arms, when in the second position, extend beyond a distal end of the connector pin.

7. The system of claim 1, wherein one or both of the two clamping arms comprise a catch operable to engage a portion of the sleeve to axially retain the sleeve in the locked position.

8. The system of claim 1, wherein the tubular connector pin comprises a second engagement portion configured for insertion into a lumen of a second catheter such that a first portion of the second catheter surrounds the second engagement portion.

9. The system of claim 8, wherein each of the two clamping arms pivot, relative to the connector pin, at a midpoint of the clamping arm, and further wherein each of the two clamping arms comprises a second clamp portion located on a side of the midpoint opposite the clamp portion.

10. A catheter connection system comprising:
a first catheter and a second catheter each defining a lumen, each catheter comprising a first end;
a connector body comprising:
an elongate, tubular connector pin comprising a first engagement portion and a second engagement portion, the first and second engagement portions insertable into the lumens of the first and second catheters, respectively; and
two clamping arms pivotally attached near their respective midpoints to the connector pin and configured to pivot about a common pivot axis located between the first and second engagement portions, wherein each of the two clamping arms are pivotable in opposite directions between a first position, wherein first and second clamp portions of each of the two clamping arms extend outwardly and away from the first and second engagement portions, respectively, to a second position, wherein the first and second clamp portions of each of the two clamping arms contact the first and second catheters, respectively; and
first and second tubular sleeves each slidable along a longitudinal axis of the connector pin, to a locked position wherein the first and second sleeves are positioned over the first and second clamp portions, respectively, when both of the two clamping arms are in the second position, such that a lumen of each sleeve receives the two clamping arms with an interference fit and biases the two clamping arms inwardly to compress the first and second catheters against the first and second engagement portions of the connector pin, respectively.

11. The system of claim 10, wherein the two clamping arms, when in the second position, extend beyond opposite distal ends of the connector pin.

12. The system of claim 10, wherein each of the two clamping arms comprises a semi-cylindrical member that mates with the other of the two clamping arms along a plane that both contains the longitudinal axis of the connector pin, and intersects the pivot axis.

13. The system of claim 10, further comprising two shafts protruding from the connector pin in a direction normal to the longitudinal axis of the connector pin, the two shafts defining the pivot axis.

* * * * *